United States Patent [19]

Stephenson et al.

[11] Patent Number: 4,979,936
[45] Date of Patent: Dec. 25, 1990

[54] AUTOLOGOUS BIOLOGIC PUMP MOTOR

[75] Inventors: Larry W. Stephenson, Ambler; Robert L. Hammond, Prospect Park; Michael A. Acker; William A. Anderson, both of Philadelphia, all of Pa.

[73] Assignee: Trustees of the University of Pennsylvania, Philadelphia, Pa.

[21] Appl. No.: 43,487

[22] Filed: Apr. 28, 1987

[51] Int. Cl.$^5$ .................. A61M 1/10; A61M 1/362
[52] U.S. Cl. .................................. 600/16; 623/3
[58] Field of Search ............... 628/419 R; 600/16, 17, 600/18; 128/64; 623/3

[56] References Cited

U.S. PATENT DOCUMENTS

| | | | |
|---|---|---|---|
| 4,192,293 | 3/1980 | Asrican | 600/17 |
| 4,453,537 | 6/1984 | Spitzer . | |
| 4,813,952 | 3/1989 | Khalafalla | 623/3 |
| 4,919,661 | 4/1990 | Gibney | 623/3 |

OTHER PUBLICATIONS

Macoviak, J. A., Stephenson, L. W., et al., "Electrophysiological and Mechanical Characteristics of Diaphragmatic Autograft Used to Enlarge Right Ventricle," 31 Surgical Forum 270 (1980).
Macoviak, J. A., Stephenson, L. W., et al., "Replacement of Ventricular Myocardium With Diaphragmatic Skeletal Muscle," 81(4) J. Thoracic & Cardiovascular Surg. 519 (1981).
Macoviak, J. A., Stephenson, L. W., et al., "Effect of Electrical Stimulation on Diaphragmatic Muscle Used to Enlarge Right Ventricle," 90(2) Surgery 271 (1981).
Macoviak, J. A. Stephenson, L. W., et al., "Partial Replacement of the Right Ventricle with A Synchronously Contracting Diaphragmatic Skeletal Muscle Autograft," 5(Suppl.) Artificial Organs 550 (1981).
Macoviak, J. A., Stephenson, L. W., et al., "Electrical Conditioning of In Situ Skeletal Muscle for Replacement of Myocardium," 32 J. Surg. Research 429 (1982).
Armenti, F. R., Bitto, T., et al., "Transformation of Canine Diaphragm to Fatigue-Resistant Muscle by Phrenic Nerve Stimulation," 35 Surg. Forum 258 (1984).
Armenti, F. R., Bitto, T., et al., "Conditioning of Skeletal Muscle for Myocardial Replacement," VIII Biotelemetry 283, Doring Publishing Co., Braunschweig, West Germany (1984).
Hoffman, B. K., Gambke, B., et al., "Myosin Transitions in Chronic Stimulation Do Not Involve Embryonic Isozymes," 8 Muscle & Nerve 796 (1985).
Bitto, T., Mannion, J. D., et al., "Prectoralis and Rectus Abdominus Muscles for Potential Correction of Congenital Heart Defects," *Pediatric Cardiology-Proceedings of the Second World Congress* 609, Springer-Verlag, New York (1986).
Bitto, T., Armenti, F. R., et al., "Time Course of Transformation of Dog Diaphragm Muscle with Continuous Low Frequency Stimulation at 10 Hertz and 2 Hertz," *Proceedings of 2nd Vienna Muscle Symposium*, Jun. 14–15, 1985, 175 (1986).

(List continued on next page.)

*Primary Examiner*—David J. Isabella
*Assistant Examiner*—Stephanie L. Iantorno
*Attorney, Agent, or Firm*—Woodcock, Washburn, Kurtz, Mackiewicz & Norris

[57] ABSTRACT

An apparatus and method for use in assisting a human heart is disclosed. A skeletal muscle is formed into a pouch which then surrounds a collapsible, shape-retaining bladder. The bladder is connected to a second bladder enclosed in a sheath around a portion of the aorta. The bladders are filled with a fluid such that when the skeletal muscle contracts in response to an electrical stimulation, the fluid is forced from the first bladder into the bladder sheathed with the aorta, expanding that bladder and forcing the aorta to compress.

A period of vascular delay and electrically stimulated training is preferred after the pouch is formed and before use in conjunction with the aorta. Use of a gate means between the two bladders enables implantation of the entire system in one surgical procedure.

53 Claims, 2 Drawing Sheets

OTHER PUBLICATIONS

Mannion, J. D., Bitto, T., et al., "Histochemical and Fatigue Characteristics of Conditioned Canine Latissimus Dorsi Muscle," 58(2) Circulation Res. 298 (Feb. 1986).

Mannion, J. D., and Stephenson, L. W., "Potential Uses of Skeletal Muscle for Myocardial Assistance," 65(3) Surgical Clinics of North Amer. 679 (1985).

Leriche, R., et al., "Essai Experimental de Traitment de Certains Infarctus du Myocarde et d'Aneurisme de coeur Par une Greffe de Muscle Strie," 59 Bull. Soc. Nat. Chir. 229 (1933).

Beck, C. S., "A New Blood Supply to the Heart by Operation," 61 S.G.O. 407 (1935).

Kantrowitz and McKinnon, "The Experimental Use of the Diaphragm as an Auxiliary Myocardium," 9 Surg. Forum 266 (1959).

Petrovsky, G. V., "Surgical Treatment of Cardiac Aneurysms," 41 J. Thoracic & Cardiovascular Surg. 438 (1961).

Dewar, M. L., et al., "Synchronously Stimulated Skeletal Muscle Graft for Myocardial Repair," 87 J. Thoracic & Cardiovascular Surg. 325 (1984).

Neilson, I. R., Brister, S. J., et al., "Left Ventricular Assistance in Dogs Using a Skeletal Muscle Powered Device for Diastolic Augmentation," IV(3) Heart Transplantation 343 (1985).

Mannion, J. D., Hammond, R., and Stephenson, L. W., "Hydraulic Pouches of Canine Latissimus Dorsi Potential For Left Ventricular Assistance," 91(4) J. Thoracic & Cardiovascular Surg. 534 (Apr. 1986).

Bitto, T., Mannion, J. D., et al., "Preparation of Fatigue-Resistant Diaphragmatic Muscle Grafts for Myocardial Replacement," *Progress in Artificial Organs —1985*, 441, ISAO Press (1986).

Stephenson, L. W., Macoviak, J. A., et al., "Skeletal Muscle for Potential Correction of Congenital Heart Defects," *Biomedical Cardiac Assist—Cardiomyoplasty and Muscle Powered Devices*, Chiu, R. C. J., Ed., Futura Publishing, Chapter 10 (1986).

Acker, M. A., Mannion, J. D., et al., "Methods of Transforming Skeletal Muscle Into a Fatigue-Resistant State: Potential for Cardiac Assistance," *Biomedical Cardiac Assist—Cardiomyoplasty and Muscle Powered Devices*, Chiu, R. C. J., Ed., Futura Publishing, Chapter 2 (1986).

Acker, M. A., and Stephenson, L. W., "Skeletal Muscle for Heart Repair or Assistance," 1(3) Cardiac Chronicle 1 (Apr. 1986).

Neilson, J. R., and Chiu, R.C.J., "Skeletal Muscle-Powered Cardiac Assist Using an Extra-Aortic Balloon Pump," *Biomedical Cardiac Assist—Cardiomyoplasty and Muscle Powered Devices*, Chiu, R. C. J. Ed., Futura Publishing, Chapter 11 (1986).

Mannion, J. D., Velchik, M., et al, "Transmural Blood Flow of Multi-Layered Latissimus Dorsi Skeletal Muscle Ventricles During Circulatory Assistance," 32(1) ASAIO Transactions 454 (Jul.–Sep. 1986).

Acker, M. A., Hammond, R. L., et al., "Non-Preconditioned Skeletal Muscle Pump Motor: One Week Experience," 4 (Supp. 2) Life Support System—J. Europ. Soc. Artif. Org. 18 (Sep. 1986).

Acker, M. A., Hammond, R. L., et al., "An Autologous Biologic Pump Motor," 92 J. Thoracic & Cardiovasc. Surg. 733 (Oct. 1986).

Mannion, J. D., Acker, M. A., et al., "Four Hour Circulatory Assistance With Canine Skeletal Muscle Ventricles," 37 Surg. Forum 211 (Oct. 1986).

Acker, M. A., Anderson, W. A., et al., "Oxygen Consumption of Fatigue-Resistant Muscle," Program of Annual Meeting—Amer. Assn for Thoracic Surgery, Apr. 6–8, 1987, p. 42.

Acker, M. A., Hammond, R. L., et al., "Skeletal Muscle as the Potential Power Source for a Cardiovascular Pump: Assessment in Vivo," 236 Science 324 (Apr. 17, 1987).

Altman, L. K., "Muscle Fashioned Into Auxiliary Heart in Dog," 137 New York Times, Dec. 10, 1986, at A1.

Altman, L. K., "Dogs' Deaths Halt Tests on Hearts," New York Times, Feb. 9, 1987, at C4.

Acker, M. A., Mannion, J. D., etal., "Canine Diaphragm Muscle After 1 yr of Continuous Electrical Stimulation: Its Potential as a Myocardial Substitute," 62(4) J. Applied Physio. 1264 (Apr. 1987).

Spirit of Enterprise—The 1987 Rolex Awards, "Rebuilding a Heart From a Skeletal Muscle—Larry Warren Stephenson."

Mannion, J. D., Acker, M. A., et al., "Power Output of Skeletal Muscle Ventricles in Circulation: Short-Term Studies," 76(1) Circulation 155 (Jul. 1987).

Acker, M. A., Anderson, W. A., et al., "Skeletal Muscle Ventricles in Circulation," 94(2) J. Thoracic & Cardiovasc. Surg. 163 (Aug. 1987).

Letter to Bill Anderson from Eldon E. Frisch, dated Sep. 18, 1986.

Letter to Larry W. Stephenson from John T. Watson dated Feb. 6, 1987.

AUTOLOGOUS BIOLOGIC PUMP MOTOR

"This invention was made with government support under a grant awarded by the Department of Health and Human Services. The U.S. Government has certain rights in this invention."

BACKGROUND OF THE INVENTION

1. Field of The Invention

The present invention relates to the field of biologic pump motor mechanisms. More specifically, it relates to an improved method for assisting the human heart in pumping blood to the body.

2. Description of the Prior Art

Heart failure is one of the leading causes of death in the United States, and is frequently caused by heart attacks. Heart attacks are most commonly caused when arteries supplying blood to a portion of the heart become blocked, resulting in that portion of the heart muscle dying off. The heart's left ventricle is its main pumping chamber. If a heart attack of any size occurs there, it will likely be fatal. If the area of heart muscle involved is not too large, the person will survive and that portion of the heart muscle will eventually become non-functioning scar tissue.

There are currently an estimated 10,000 patients in the United States annually suffering with irreversible congestive heart failure secondary to myocardial fibrosis. In such cases, the damaged heart may pump only a fraction of the amount of blood a normal one would. Fluids back up into the lungs, the lungs become engorged, and shortness of breath occurs. The ankles as well as the abdomen may become swollen. Physical activity is limited. Patients may only be able to take a few steps before becoming short of breath. Some are confined to bed.

Unfortunately the present outlook for most of these patients is dismal. Although conventional medical therapy with digitalis and after load reducing agents results in a mortality rate of approximately 50% within one year, it is the only method of treatment available for most patients. New drugs are always being developed and tested, but it is unlikely that any will be able to cause scar tissue that was once heart muscle to contract again.

Each year, more people benefit from heart transplants; however, heart transplantation continues to be plagued by numerous problems. About half of the patients who receive heart transplants die from rejection-related problems within five years after their transplant. The drugs used to suppress rejection are associated with numerous undesirable side effects and complications. There continues to be a significant donor shortage that frequently results in long waiting periods for these desperately ill patients. 10–25% of these patients may die while on the waiting list. In addition, because of the donor shortage, patients over the age of 65 are generally not even considered for such a surgical procedure. Cost is also a significant factor.

Mechanical hearts have been tried in a relatively small group of patients, but, at the present time, are not being used as a permanent heart replacement because of complications such as infection, stroke, and mechanical pump failure. They continue to be used as a "bridge to heart transplantation" for some of the patients with end-stage heart failure, a condition that will no longer allow them to wait for a suitable donor. This sometimes can buy a week or more of time while an appropriate donor heart is being located The use of these mechanical pumps in even these cases can be controversial since other short term support techniques are available. At rest, the patients who presently use such devices are tethered by tubes and wires to a large, cumbersome, external power source. Despite the fact that large sums of money are spent on this research each year by the United States government, there is no totally implantable power source even on the horizon.

Thus, there exists a need for a method or apparatus to aid individuals suffering from irreversible congestive heart failure.

In addition, in the United States, 12,000–15,000 babies are born each year with congenital heart defects. While the majority of these defects are relatively easy to correct surgically, the ideal form of correction for some congenital heart defects, such as hypoplastic left heart syndrome, has eluded the surgeon. Thus, there exists a need for a method or apparatus to aid in correcting the problems encountered by individuals suffering from such problems.

Over the years, there have been various suggestions to use autogenous skeletal muscle to either replace or assist the failing heart. Such methods have several advantages over other forms of therapy. First of all, the skeletal muscle is not foreign to the host and, therefore, would not be subject to tissue rejection. Secondly, there would be no problem of donor shortages. Thirdly, they would obviate the necessity for a cumbersome and inefficient external power source.

In 1933, Leriche and Fontaine experimentally demonstrated the feasability of using pectoralis muscle to reinforce myocardial scar after acute ligation of the coronary artery. Leriche, R., et al. "Essai experimental de traitment de certains infarctus du myocarde et de l'aneuvrisme de coeur par une greffe de muscle strie," 59 BULL. SOC. NAT. CHIR. 229 (1933). In 1935, Beck grafted skeletal muscle to the canine heart and then gradually occluded both coronary arteries, thereafter showing that the heart was given a new source of blood. Beck, C. S., "A New Blood Supply to the Heart by Operation," 61 S.G.O. 407 (1935). Kantrowitz was the first to wrap the aorta with skeletal muscle and then attempt to stimulate it in synchrony with the heart during cardiac diastole. He used the diaphragm muscle, and although he was able to show some increase in diastolic pressure, the effects lasted for less than a minute and then the muscle fatigued. See Kantrowitz and McKinnon, "The Experimental Use of the Diaphragm as an Auxiliary Myocardium", 9 SURG. FORUM 266 (1959). Others in the field performed variations on this theme but were limited by muscle fatigue.

In 1961, Petrovsky covered left ventricular aneurysms with diaphragmatic muscle flaps in an attempt to prevent further aneurysm enlargement and to induce collateral circulation with adjacent ischemic myocardial tissue Petrovsky, G. V., "Surgical Treatment of Cardiac Aneurysms," 41, J. THORAC. & CARDIOVASC SURG. 438 (1961). Drinkwater demonstrated in acute studies that portions of the left ventricle could be replaced with skeletal muscle. When a skeletal muscle was stimulated during cardiopulmonary bypass, the left ventricle was able to generate additional pressure. Dewar, M. L., et al, "Synchronously Stimulated Skeletal Muscle Graft for Myocardial Repair," 87 J. THORAC. & CARDIOVASC, SURG. 325 (1984).

In all of this early work, the primary impediment to the use of skeletal muscle to replace damaged myocardium or to function as a cardiac assist device was skeletal muscle fatigue. In recent years, however, various researchers have discovered that the problem of fatigue can be greatly reduced through the use of electrical conditioning of skeletal muscle. See, e.g., Macoviak et al, "Electrical Conditioning of In Situ Skeletal Muscle for Replacement of Myocardium", 32 J. SURGICAL RES. 429 (1982), incorporated herein by reference.

Cardiac muscle is similar to skeletal muscle with respect to the basic structure and mechanics of contraction, and in that both are capable of transforming chemically stored energy into mechanical work. The cardiac cell differs from the skeletal muscle cell by the presence of the intercalated disc. The intercalated disc is thought to serve as a low resistance pathway to facilitate electrical current flow during excitation, allowing the myocardium to contract in on "all or none" fashion. Unlike the heart, which is an electrical and mechanical syncytium, skeletal muscle is modulated by the number and rate at which the fibers are activated A single electrical stimulus resulting in a single muscle twitch does not generate sufficient force to power a cardiac assist device. However, rapid repetitive stimuli delivered before the muscle fiber completes its relaxation results in mechanical summation until fusion occurs, which thereby causes the muscle to generate substantially greater contractive force.

In order to optimally perform different functions, skeletal muscle has differentiated into two basic types of fibers. The Type I fiber is slow-twitch, oxidative, and found in muscles that are capable of generating substantial force over a prolonged period of time. They possess a prolonged contraction time, a large mitochondrial volume, a relatively small sarcoplasmic reticulum, and a specific slow type of myosin. Most importantly, these fibers resist fatigue and rely on an aerobic metabolism. The Type II fiber is fast-twitch, glycolytic, and more frequently found in muscles that generate intense, episodic movement, such as muscles controlling eye movement. These fibers possess a brisk contraction time, small mitochondrial volume, extensive sarcoplasmic reticulum, and a specific fast myosin molecule. The fast-twitch fibers are dependent on an anaerobic metabolism and fatigue rapidly.

It has been found that skeletal muscle is capable of changing its physiologic, biochemical, and structural characteristics in response to exercise and electrical stimulation. When a muscle is electrically stimulated by its motor nerve, the entire muscle undergoes transformation to the Type I muscle fiber. This process is complete after about six weeks of continuous stimulation with frequency as low as 2 Hertz (the frequency of a resting dog's heart rate). With this in mind, it has been found that it is possible to condition skeletal muscle while it is contracting in synchrony with the heart.

A variety of skeletal muscles have been investigated for use in cardiac assistance. A group including the inventors herein have decided that the latissimus dorsi is the most appropriate. This muscle was chosen for several reasons. It is a large, powerful muscle with about the same muscle mass as the left ventricle. It is a noncritical muscle; in fact, plastic surgeons use it with impunity to replace defects in the human abdominal or chest wall caused by tumors. They also occasionally use it to enlarge women's breasts. The loss of use of the muscle causes almost no physical impairment. Although it is used to shrug the shoulder, there are other muscles that also perform the same task. The muscle is also easy to free from its natural position and to move near the heart. Finally, it has a single main blood supply and a single nerve, which, from a technical standpoint, makes it easy to work with.

As discussed earlier, the major problem of muscle fatigue can be overcome, at last partially, by a process of conditioning the muscle to be used with electrical stimulation. Recent work also showed that a delay period after the muscle to be used is formed into its new shape is very important. Prior workers in the field had begun to use the reformed muscle immediately without realizing that such immediate use dramatically affected the ability of the muscle to receive a blood supply, and therefore resist fatigue, because the forming step ligated much of the collateral blood sources. It was later found that a period of delay allowed the formed muscle to recover somewhat from the trauma of the forming operation and to develop new channels of collateral circulation.

Other problems arose in the prior art when a skeletal muscle was used to actually replace part of the heart or the aorta. One suggestion to overcome these problems was to form a hydraulic pouch with the skeletal muscle pedicle and use that pouch to power an assist device rather than to directly connect the muscle to the heart or the aorta. The potential for hydraulic pouches is reported, for example, in Mannion, J. D., et al, "Hydraulic Pouches of Canine Latissimus Dorsi—Potential for Left Ventricular Assistance", 91(4) J. THORACIC & CARDIOVASC. SURG. 534 (April, 1986), incorporated herein by reference. That paper discloses the construction of latissimus dorsi muscle pouches in the form of a multi-layered conical spiral. The experiment there was designed to determine if any combination of electrical conditioning, vascular delay, and a multi-layered pouch would minimize muscle fatigue and permit an auxiliary ventricle to assume a portion of left ventricular function.

Another group reported on using skeletal muscle as a cardiac assisting device in conjunction with an extra-aortic balloon. The muscle there was formed as a pedicle around a bladder that was connected to a T-shaped system. The T-part of the system surrounded a dacron conduit that had been connected to the aortic blood flow by anastomosis at both ends. The T-part attached to the dacron so as to form a leak-proof system which was then filled with fluid. Thus, contraction of the muscle forced more fluid into the T-part which thereby squeezed the dacron conduit and assisted the aorta in pumping. See Nielson, I. R., et al, "Skeletal Muscle-Powered Cardiac Assist Using an Extra-Aortic Balloon Pump," *Biochemical Cardiac Assist—Cardiomyoplasty and Muscle Powered Devices*, Chiu, R. C. J., Ed., Futura Publishing, 19 (1986).

Despite all of the advances of the prior art, the solutions provided so far suffer from several problems. Either direct transection or anastomosis of the aorta is necessary (as in the previous paragraph) with all of the dangers incumbent upon such a procedure (interruption of blood flow, risk of infection, etc.) or no adequate method has been developed for using the idea of a muscle pouch in conjunction with a hydraulic pump system, or both. Further, if training of a skeletal muscle is needed, a series of operations have been required, multiplying all of the risks attending surgery.

Accordingly, there exists a need for an apparatus usable as an autologous biologic pump motor to assist in blood circulation, usable for an extended period of time, that avoids the dangers of both transection or anastomosis of the aorta and multiple operations.

SUMMARY OF THE INVENTION

The present invention is directed to an autologous biologic pump motor utilizing a skeletal muscle to assist in human, or other mammal, blood circulation.

According to the present invention, a skeletal muscle is formed as a pedicle into a conical hydraulic pouch, leaving the end containing the primary source of blood supply and main motor nerve attached, and a bladder is inserted into the hydraulic pouch. This bladder is connected by a hollow connecting means to a second bladder located adjacent to a circulatory organ requiring assistance. A portion of that organ as well as the second bladder are enclosed within a sheath such that when the second bladder expands it forces the organ to contract, thereby assisting the organ in pumping. The system formed by the two bladders and the connecting means is then filled with a fluid or gas and an electrical pacer is attached to the motor nerve of the skeletal muscle to stimulate the muscle into contraction in synchrony with the organ to be assisted. When the muscle contracts it squeezes the first bladder forcing the fluid or gas through the connecting means and into the second bladder. The second bladder is forced to expand, thereby compressing the adjacent organ. Typically, a period of delay followed by a period of electrical stimulation training occurs after the muscle pedicle is formed into the pouch but before it is used in conjunction with the organ to be assisted. This prepares the muscle for its new function as a circulatory assistant.

Additionally, a gate means is placed in the connecting means such that the flow of fluid from one bladder to another can be controlled. Closing this gate initially will allow for the training of the skeletal muscle while in place without forcing the muscle to coordinate and work with the aorta. Using a gate means, known to those in the art, that can be opened while the system is implanted, the entire biologic pump system can be set up and implanted in a single surgical procedure, avoiding all of the hazards associated with multiple operations or with devices that are not fully implantable.

Accordingly, it is an object of the present invention to provide an apparatus for use as a fully implantable autologous biologic pump motor to assist in human circulation and a method for effectively using that biologic pump motor. Other and further objects and advantages will appear hereinafter.

DETAILED DESCRIPTION OF THE PREFERRED EMBODIMENTS

A unique and inventive apparatus for use as an autologous biologic pump motor has been discovered. While such an apparatus could be used with a variety of circulatory systems and in a variety of animals, the most preferred use is to assist a human being suffering from irreversible congestive heart failure. In such a situation, the disclosed invention would preferably be used to assist a human aorta in pumping an adequate supply of blood to the human body.

Figure 1:
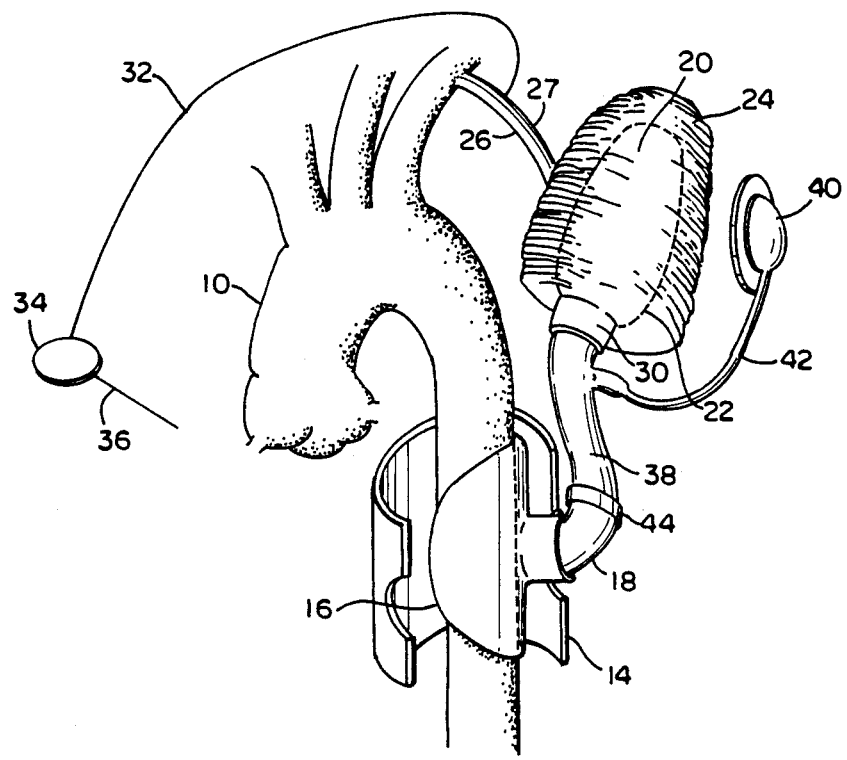
FIG. 1 is a schematic diagram illustrating a preferred embodiment of the autologous biologic pump motor of the present invention.

Turning in detail to the drawings, FIG. 1 illustrates such an embodiment of the present invention. A human aorta 10 emanates from the left ventricle of the human heart. A cylindrical portion of the aorta 10 is enclosed in a circumferential sheath 14. This sheath 14 also encloses a bladder 16. The sheath 14 can be made of any non-elastic, biocompatible material. In a preferred embodiment, however, the sheath is made of a highly flexible material such as a Dacron TM weave material. The bladder 16 can be made of any leak-proof, material, preferably silastic or polyurethane. In another embodiment, the bladder is made of an elastic material so that, if it is expanded, it has a tendency to snap back to its original shape upon release of the expanding pressure.

The sheath 14 encloses the bladder 16 and the aorta 10 within a defined space. Thus, if the bladder 16 expands within the sheath 14, it will press against the aorta 10 and force the enclosed portion of the aorta to compress.

Figure 2:
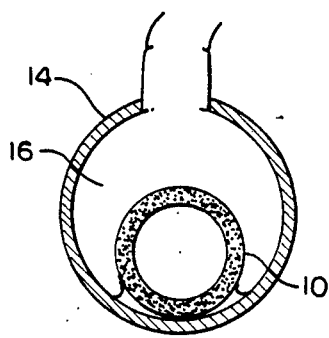
FIG. 2 illustrates in cross-section an embodiment of the arrangement of the first bladder in conjunction with the aorta.
Figure 3:
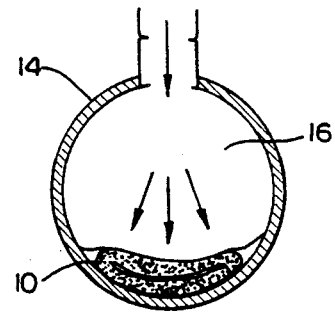
FIG. 3 illustrates in cross-section the embodiment of the arrangement of the first bladder in conjunction with the aorta of FIG. 2 after expansion of the first bladder
Figure 4:
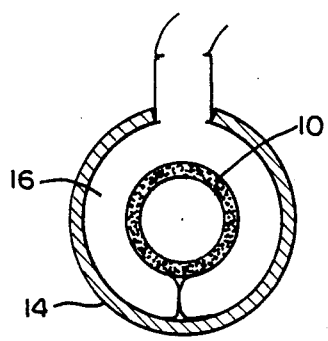
FIG. 4 illustrates in cross-section another embodiment of the arrangement of the first bladder in conjunction with the aorta.
Figure 5:
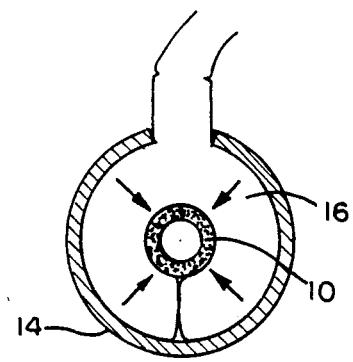
FIG. 5 illustrates in cross-section the embodiment of the arrangement of the first bladder in conjunction with the aorta of FIG. 4 after expansion of the first bladder.

The configuration of the bladder 16 and the aorta 10 within the sheath 14 may be any one of a variety of configurations. As shown in FIG. 2, for example, the bladder 16 may be located adjacent to the aorta 10 such that the two only abut on one side. FIG. 3 shows this configuration after expansion of bladder 16. An alternative embodiment, as shown in FIGS. 4 and 5, would have the bladder 16 wrapped circumferentially around the aorta 10 between the aorta 10 and the sheath 14. Thus, when the bladder 16 expands within the sheath 14, it exerts pressure inwardly on all sides of the aorta 10, forcing the aorta 10 to compress evenly on all sides.

The bladder 16 is connected to a connector 18 which comprises a hollow tube. Again, the composition of the connector 18 is not critical so long as it is biocompatible and, in this case, is substantially inelastic in comparison to the bladder 16.

The connector 18 is, in turn, connected to a second bladder 20. This second bladder 20 is composed of any leak-proof material in the same manner as the bladder 16. In one embodiment, the second bladder 20 is composed of a shape-retaining material such that if it is forced to collapse it will have a tendency to return to its original shape when the collapsing force is removed. The bladder 16 and the second bladder 20 can be any of a wide variety of shapes. A preferred embodiment has both of these bladders shaped like sausages, i.e., roughly cylindrical with rounded edges.

Figure 6:
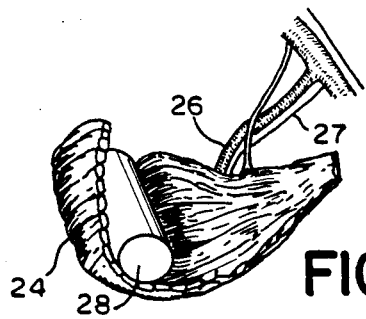
FIG. 6 is a schematic diagram showing the pouch-forming step of the method of the present invention.
Figure 7:
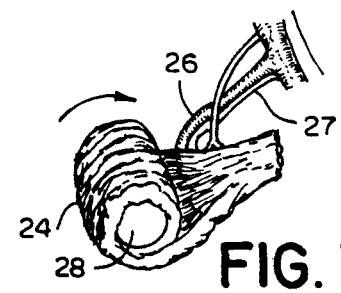
FIG. 7 is a schematic diagram showing the completion of the pouch-forming step using a mandrel of the method of the present invention.

The second bladder 20 is inserted within a pouch 22 formed by a skeletal muscle 24. Any suitable skeletal muscle can be employed such as the rectus abdomenis, pectoralis, latissimus dorsi, psoas, or diaphragm. A preferred embodiment uses the latissimus dorsi. The skeletal muscle 24 is a pedicle that has been partially detached from the rest of the body but remains connected at one end having a primary source of blood supply 26 as well as the main motor nerve 27. After the collateral blood vessels to the skeletal muscle 24 are ligated and divided and the muscle is mobilized, it is formed into a pouch shape suitable for the insertion of a bladder 20. Such a forming procedure is preferably performed by using a mandrel 28 as shown in FIGS. 6 and 7. The skeletal muscle 24 is wrapped around the mandrel 28, the mandrel being formed in a shape preferred for the pouch 22. The mandrel 28 can be composed of any suitable material, as known to those of ordinary skill in the art, with a preferred embodiment being made of Teflon TM. Once the skeletal muscle 24 is adequately formed such that a pouch 22 exists and will retain its shape, the mandrel 28 can be removed and replaced with the second bladder 20. While a preferred embodiment of the pouch 22 formed by the skeletal muscle 24 is a cone, different configurations would certainly be operable and may depend upon the muscle chosen. In another embodiment, the pouch 22 would be spherical in shape with the second bladder 20 having a corresponding shape. Further, the amount of power produced by the biologic pump motor can be varied by varying the number of times that the skeletal muscle 24 is wrapped around the mandrel 28 during the forming procedure. The more wraps involved, the thicker the muscle becomes and the more powerful the biologic pump motor. A preferred embodiment involves wrapping the skeletal muscle 24 approximately 2-2½ times around the mandrel 28.

In a preferred embodiment, a flexible collar 30 is attached by sutures to the formed skeletal muscle 24 immediately after forming. Such a collar can be made of any suitable material such as a Teflon TM felt. The collar 30 is preferably attached to the tendonous margin of the skeletal muscle 24 for maximum durability. Over time, the skeletal muscle 24 grows around the collar 30 so that the collar 30 becomes intimately bound to the formed muscle. Initially, the collar 30 can act to maintain the mandrel 28 in place. The collar 30 can then act as a means to connect the later system apparatus and to maintain that system in proper position. Further, it aids to preventing shrinkage of the muscle pouch 22 over time.

An electronic pacing system comprised of an electrode 32 attached to the motor nerve 27, a pacer 34, and a second electrode 36 attached to the heart in an appropriate manner, enables stimulation of the skeletal muscle 24 in synchrony with the heart. The pacer 34 is capable of providing adequate stimulation to the skeletal muscle 24 to force it to contract. Given the nature of the skeletal muscle 24, as discussed in the Background above, a preferred pacer 34 is capable of providing stimulation in the form of pulse trains to efficiently generate forceful muscle contractions. Further, the muscle is most effectively stimulated via its motor nerve 27 rather than directly.

The system composed of the two bladders, 16 and 20, and the connector 18 is filled with a fluid or gas 38. This fluid or gas 38 can be any fluid or gas but should preferably be biocompatible In one embodiment, the fluid 38 is a saline solution.

While not a necessary component of the system, a preferable addition is a pressure port 40 connected to the connector 18 by a hollow tube 12. This pressure port 40 can be used to adjust the amount of fluid or gas 38 in the system and thereby adjust the pressure within the system.

In operation, the electronic pacer 34 correlates to the beat of the heart and stimulates the motor nerve 27 and thereby the skeletal muscle 24 into contraction through the electrode 32. This stimulation should be a pulse train since the skeletal muscle 24 would not contract in toto in response to a single electrical stimulation. The burst pattern is typically in the range of 10–85 Hertz with the burst comprising from one quarter to one third of the total duty cycle. Certain pacers 34 may actually capture the heartbeat.

When the muscle 24 contracts, it collapses the second bladder 20 contained within the pouch 22, thereby forcing some of the fluid or gas 38 contained within the second bladder 20 out through connector 18 and into the bladder 16. This excess fluid or gas forces the bladder 16 to expand within the sheath 14 and thereby compresses the enclosed portion of aorta 10. When the electrical stimulation ceases, skeletal muscle 24 relaxes. This relaxation exerts an outward tension on bladder 20, encouraging it to expand to its original shape. Further, in particular embodiments, the elasticity of bladder 16 exerts a pressure on the excess fluid and gas now contained in the bladder 16, pushing that fluid or gas back through connector 18 and into bladder 20. Also, any shape-retaining characteristic of the second bladder 20 will exert a force sucking the fluid or gas back into the second bladder 20. This process is aided by any pressure within the aorta 10 that would push against bladder 16 within sheath 14.

Thus, through stimulation of skeletal muscle 24, a portion of aorta 10 is periodically compressed. This periodic compression is preferably synchronized with the period of the heart so that the aortic compression occurs during the diastole of that heart. This particular synchronization is the most efficient and it also allows blood to flow to the skeletal muscle 24 while it is in a relaxed state. The advantages of such a system are numerous. The compression of the aorta 10 acts to pump blood and thereby aid the heart in performing its duties. Further, during the relaxation stage, the action of the system returning to its original shape creates a modest negative pressure within the contracted portion of the aorta 10, thereby sucking more blood from the heart into that section of the aorta, easing the heart's workload. Such a system also acts to raise the diastolic pressure of the individual, an advantage to those suffering from congestive heart failure.

There are numerous variations on the preferred embodiment described above contemplated to be covered by the present invention. For example, the bladder 16 can be constructed such that one portion of it is more easily deformable than another. Thus, when the excess fluid or gas 38 is forced into the bladder 16, one portion would expand before another. This can be used to channel blood flow in one direction.

Further, the fluid or gas 38 should be selected such that a desired flow resistance is achieved. A higher flow resistance would tend to flatten out the effect of the periodic muscle contraction, weakening its affect and extending its duration at the same time. In addition, the volume of the fluid or gas can be varied using the pressure port 40. The fuller the system, the more quickly the affect of a muscle contraction would be felt within the sheath 14. Other factors will also affect the rate of flow between the two bladders and, therefore, the amplitude and duration of the pump stroke. These parameters can include the length of the connecting tube 18 and the flow resistance between the fluid 38 and the other components of the system.

While it is important to achieve synchrony between the heart and the electronic pacer 34 and thereby the biologic pump motor, it is not necessary that the biologic pump motor contract as often as the heart. The skeletal muscle 24 can be stimulated in any pattern, for example once every two heartbeats, so long as it is in synchrony with the period of the heart. Limiting the stimulation of the skeletal muscle 24 to a less than 1:1 ratio with respect to the heart period might have important ramifications with respect to muscle fatigue and can also be used to regulate the amount of assistance given to the circulatory system.

One of the primary advantages of the present invention is that the apparatus as described is capable of being totally implantable within the body. Even the pressure port 40 can be located subcutaneously, reachable by a needle if necessary. There is no necessity for an external power source and, further, and most importantly, there is no need to transect or perform anastomosis on any portion of the aorta. Since there is no transection or anastomosis and nothing crosses the skin after the initial implantation, the risk of infection is minimized, and the trauma associated with multiple operations or with any operation directly on the heart or the aorta is avoided. This is a substantial improvement over most prior art devices.

While the apparatus as disclosed above is operable, without the use of a specialized methodology the skeletal muscle 24 may quickly fatigue. The collateral ligation of the skeletal muscle 24 occurring during the pouch forming step cuts off much of the blood flow to the skeletal muscle 24. By allowing for a period of vascular delay subsequent to the forming procedure, the skeletal muscle 24 is able to partially recover from the procedure and even form new secondary sources of blood supply. Thus, a period of rest is preferable. In a preferred embodiment, the rest period is at least two weeks and preferably approximately three to four weeks long.

In addition to the rest period, it has also been found, as was discussed in the Background above, that it is advantageous to train and condition the skeletal muscle 24 after it is formed into the pouch 22 to make it more fatigue-resistant. This training involves periodic electrical stimulation through the electrode 34 and motor nerve 27 prior to the apparatus being used in conjunction with the aorta 10. The training period acts to convert the skeletal muscle from a Type II, fast-twitch, fatiguable muscle to a Type I, slow-twitch, fatigue-resistant muscle. A burst pattern should be used with a preferred burst pattern range being 10-85 Hertz. These bursts should make up approximately one quarter to one third of each duty cycle and the rate of duty cycles should preferably be 30-120 per minute. While the timing and amount of training can also be varied, a preferred embodiment involves training for approximately 3-6 weeks. Further, while the concept of training the skeletal muscle 24 is critical, it is not necessary that the training occur prior to the apparatus being used in conjunction with the aorta 10. So long as there is a period of rest after the pouch-forming step, it is possible that the training step can be completed while the system is in actual operation assisting the human aorta 10. If this method is followed, the system should be carefully monitored so that the skeletal muscle 24 is not overloaded before it converts to a fatigue-resistant, Type I muscle. Adjusting the rate of stimulation to a period that is at a less than 1:1 ratio to the heartbeat can ease the workload on the muscle 24.

In an important variation on the embodiment described above, an adjustable gate means 44 can be provided in connector 18. Such a gate means 44 would prevent the flow of any fluid 38, or at least of any excess fluid 38, into the bladder 16. A wide variety of gate means are known to those of ordinary skill in the art that can be controlled, broken, or opened indirectly after the system has been implanted. These might include a burstable membrane, a magnetically controlled gate, or dissolvable member. Thus, the entire system can be set up in the same surgical procedure that the skeletal muscle pouch is formed. Both bladders, 16 and 20, connector 18, the pacing system, and the sheath 14, can all be implanted at the same time that the pouch is formed. Bladder 20 car than be filled with sufficient fluid that it can act as a stint for the pouch 22. The gate means 44 will prevent flow of any fluid 38 from second bladder 20 to bladder 16 during the rest period prior to use. This method negates the need for a mandrel 28, thereby eliminating the need for any further operation to remove that mandrel 28. If desired, the gate means 44 can remain closed and the skeletal muscle can be trained and conditioned while implanted but prior to the normal operation of the apparatus in conjunction with the aorta 10. When desired, the gate means 44 can be opened.

Figure 8:
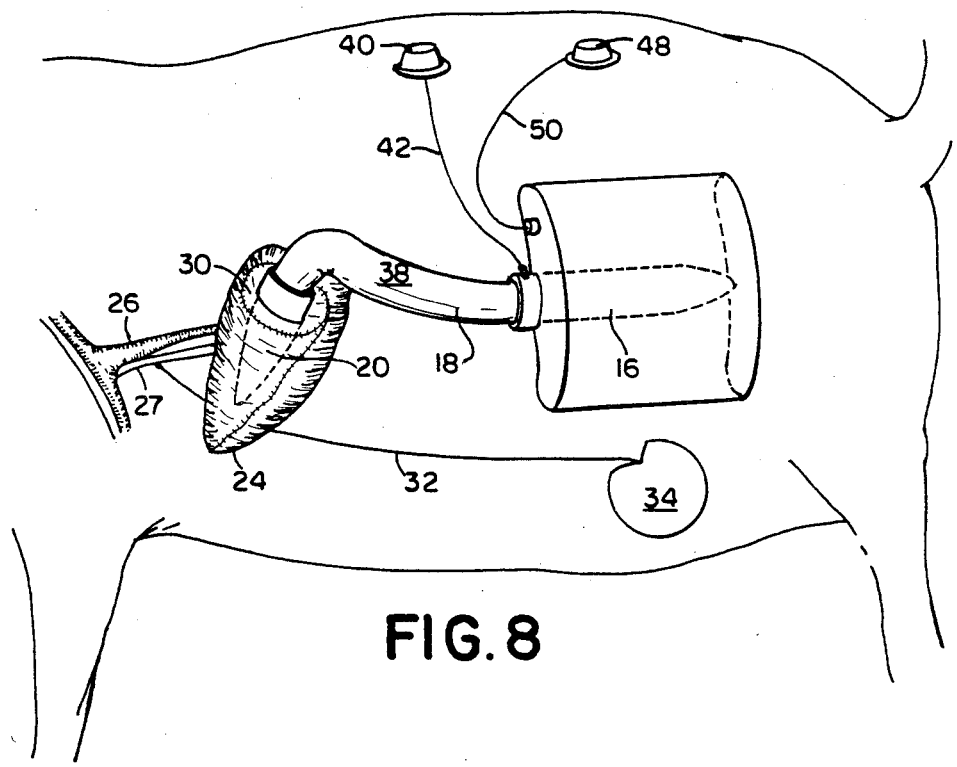
FIG. 8 is a schematic diagram illustrating a mock circulation system implanted according to the present invention.

While use of the apparatus and method of the present invention to directly assist an actual circulation system is the preferred embodiment, the apparatus of the present invention can also be adapted for use with a mock circulation system to assist in research. As shown in FIG. 8, such an apparatus would involve a skeletal muscle 24, two bladders 16 and 20, a connector 18 with a collar 30, an electrode 32 connected to a motor nerve 27, an electronic pacer 34 connected to the electrode 32, and a fluid or gas 38 contained within the system. In this embodiment, however, the first bladder 16 is enclosed within an airtight canister 46. The electrically stimulated skeletal muscle 24 contracts in the same manner and squeezes bladder 20, forcing the fluid or gas 38 through connector 18 and into bladder 16. The bladder 16 expands within the airtight canister 46. A pressure port 40 can be connected to the enclosed system by means of a hollow tube 42 in the same manner as in the embodiments described above. A second pressure port 48 can be connected to the airtight canister 46 by a second hollow tube 50 whereby the pressure and/or volume of gas within the airtight canister 46 can be controlled. By controlling the volume and pressure of the gas within the airtight canister 46, the amount of work that must be performed by the muscle 24 to expand the bladder 16 can also be controlled or measured. Once again, the entire system is totally implantable, and successful operations implanting such devices have been performed on dogs whereby the dogs showed no sign of physical discomfort with the implanted device.

One of ordinary skill in the art would recognize that the above-disclosed invention can be used with any variety of mammals and has possible uses with a variety of circulatory systems. While the embodiment disclosed involves the human aorta, it is also possible to use the apparatus in conjunction with the pulmonary artery and all such variations are contemplated as within the scope of the present invention.

Because of the fact that a few weeks are typically necessary for the recovery of collateral muscle blood supply before the biologic pump can be effectively activated, such systems are less suitable for patients of cardiogenic shock from acute myocardial infarction. However, many people have chronic heart failure caused by diseases of the heart muscle, including previous heart attacks.

Thus, a totally implantable autologous biologic pump motor for assisting human circulatory systems is disclosed that employs a skeletal muscle formed into a pouch. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An implantable biologic pump motor apparatus comprising:
   an autologous skeletal muscle pedicle having two ends, a first end with an attached main motor nerve and a primary source of blood supply and a second end formed to create a muscle pouch having a cavity;
   a collapsible bladder inserted into said cavity;
   an expandable bladder located adjacent to a portion of a system requiring a pump;
   a sheath enclosing said expandable bladder and said portion located adjacent to said expandable bladder such that when the expandable bladder enclosed in the sheathing is expanded pressure is exerted on the enclosed portion whereby said portion is compressed;
   a hollow connecting means connecting said collapsible bladder and said expandable bladder to form a closed system;
   a stimulating means capable of stimulating said autologous muscle either directly or through the motor nerve such that said muscle pouch contracts; and
   a fluid or gas contained within said closed system whereby when said stimulating means stimulates said autologous muscle said muscle pouch contracts and squeezes said collapsible bladder, forcing said fluid or gas contained in said collapsible bladder though said connecting means and into said expandable bladder, expanding said expandable bladder and compressing said portion enclosed in said sheath and when said stimulating means stops stimulating the muscle said muscle pouch relaxes and the pump apparatus and the portion enclosed in said sheath returns to their uncompressed condition.

2. The apparatus of claim 1 wherein the autologous skeletal muscle is chosen from the group consisting of the latissimus dorsi, rectus, pectoralis, psoas, and diaphragm.

3. The apparatus of claim 1 further comprising an adjustable gate means in said hollow connecting means whereby the flow to the expandable bladder can be controlled or blocked, capable of being opened indirectly after the apparatus is implanted.

4. The apparatus of claim 3 wherein the gate means is chosen from the group consisting of a burstable membrane, a magnetically controlled valve, and a dissolvable member.

5. The apparatus of claim 1 further comprising a flexible collar attached to said formed muscle pouch around the opening of said cavity and also attached to said closed system.

6. The apparatus of claim 1 wherein the cavity is cone-shaped.

7. The apparatus of claim 1 wherein the cavity is spherical.

8. The apparatus of claim 1 wherein the expandable bladder is constructed of an elastic, leak-proof material.

9. The apparatus of claim 1 wherein the collapsible bladder is constructed of a shape-retaining, leak-proof material.

10. The apparatus of claim 1 wherein the expandable bladder located adjacent to the portion of the system requiring a pump abuts on only one side of said portion.

11. The apparatus of claim 1 wherein the expandable bladder located adjacent to the portion of the system requiring a pump is wrapped around said portion such that when the expandable bladder expands it exerts pressure on substantially the entire circumference of said portion.

12. The apparatus of claim 1 wherein the sheath is made of a highly flexible, inelastic material.

13. The apparatus of claim 1 wherein the hollow connecting means is substantially less elastic than either of said expandable bladder or said collapsible bladder.

14. The apparatus of claim 1 wherein the stimulating means is an electrical pacer capable of delivering pulse trains in synchrony with the period of a mammalian heartbeat.

15. The apparatus of claim 1 wherein said fluid or gas is chosen to provide a preselected flow resistance between the expandable bladder and the collapsible bladder.

16. The apparatus of claim 1 wherein said expandable bladder is constructed such that a section of said expandable bladder adjacent to a first end of said portion will expand at a lower internal pressure than a section of said expandable bladder at a second end of said portion.

17. The apparatus of claim 1 further comprising a means for adding or removing fluid or gas to or from the closed system.

18. An implantable apparatus for use in assisting a human with a heart and an aorta comprising:
   an autologous latissimus dorsi muscle having two ends, a first end with an attached main motor nerve and a primary source of blood supply and a second end formed into a muscle pouch to create a cone-shaped cavity;
   a collapsible, shape-retaining, leak-proof bladder inserted in said cavity;
   an expandable, elastic, leak-proof bladder located adjacent to a portion of said aorta;
   a flexible, non-elastic sheath enclosing said expandable bladder and said portion of aorta such that when the expandable bladder expands the portion of aorta is forced to contract;
   a hollow, non-elastic, leak-proof connecting means connecting said collapsible bladder and said expandable bladder to form a closed system;

a gate means located within said connecting means capable of controlling the flow through the connecting means and of being opened indirectly after the apparatus is implanted;

an electrical pacing means attached to said motor nerve to stimulate said muscle with electrical pulse trains in order to make said muscle contract in synchrony with the heart;

a fluid or gas contained within said closed system; and a means connected to said closed system whereby fluid or gas can be added to, or removed from, said system whereby when said electrical pacing means stimulates said muscle said muscle pouch contracts, collapsing the collapsible bladder and forcing liquid or gas through the connecting means if said gate means is open into said expandable bladder, expanding said expandable bladder and compressing said portion of aorta and further whereby when the electrical pacing means ceases to stimulate the muscle the collapsible bladder returns to its uncollapsed state, the expandable bladder returns to its unexpected state, and the portion of aorta returns to its uncompressed state.

19. The apparatus of claim 18 further comprising a flexible collar attached to said muscle pouch surrounding said cavity and also attached to said closed system.

20. The apparatus of claim 18 wherein the expandable bladder abuts only one side of said portion of the aorta.

21. The apparatus of claim 19 wherein the expandable bladder is wrapped around said portion of the aorta.

22. A method for improving the flow rate in a mammalian circulatory system having a mammalian heart comprising the steps of:

forming one end of an autologous skeletal muscle pedicle of said mammal to create a cavity within said formed muscle and leaving a second end of said muscle having a motor nerve and a primary source of blood supply attached;

inserting a collapsible bladder into said cavity;

forming a sheath around a portion of the circulatory system to form an enclosed portion and enclosing within that sheath an expandable bladder such that when said expandable bladder is expanded within the sheath the enclosed portion is forced to compress;

connecting said collapsible bladder to said expandable bladder using a hollow connector to form a closed system;

filling the closed system with a fluid or gas such that when the collapsible bladder is collapsed, said fluid or gas is forced into the expandable bladder which thereby expands;

attaching a stimulating means to said motor nerve whereby said muscle will contract upon adequate stimulation from said stimulating means;

stimulating said nerve periodically with the stimulating means, thereby making the muscle contract, collapsing the collapsible bladder, forcing the fluid or gas in said collapsible bladder through the connector and into the expandable bladder, thereby expanding the expandable bladder and compressing the enclosed portion of the circulatory system; and alternating said periodic stimulation with periods of non-stimulation so that the muscle will cease contracting, the collapsible bladder will return to its uncollapsed state, the expandable bladder will return to its unexpanded shape, and the enclosed portion will return to its uncompressed state.

23. The method of claim 22 wherein the enclosed portion of the circulatory system is a portion of the aorta.

24. The method of claim 22 further comprising the step of waiting for a period of more than two weeks either before inserting the collapsible bladder into the cavity or before performing the stimulating step.

25. The method of claims 23 or 24 wherein the stimulating step is repeated at intervals corresponding to the diastole period of a mammalian heart.

26. The method of claim 22 wherein the stimulating step occurs at a less than 1:1 ratio to the period of the mammalian heartbeat.

27. The method of claim 22 further comprising the steps of:

forming the muscle around a mandrel;

allowing the formed muscle to rest for at least two weeks with the mandrel in place; and removing the mandrel prior to inserting the collapsible bladder.

28. The method of claims 22 further comprising the step of periodically stimulating the formed muscle for a period of up 3-6 weeks prior to connecting the collapsible bladder to the bladder.

29. The method of claim 22 wherein the expandable bladder is not enclosed within the sheath until at least two weeks after the muscle is formed to create the cavity.

30. The method of claims 22, 27, or 29 further comprising the step of periodically stimulating the formed muscle for a period of 3-6 weeks prior to enclosing the bladder within the sheath.

31. The method of claim 22 wherein the mammal is a human being.

32. The method of claim 22 wherein the autologous skeletal muscle is chosen from the group consisting of the latissimus dorsi, rectus, pectoralis, psoas, and diaphragm.

33. The method of claim 22 wherein the cavity is cone-shaped.

34. The method of claim 22 wherein the cavity is spherical.

35. The method of claim 22 further comprising an adjustable gate means in said hollow connector capable of being opened indirectly should the apparatus used be implanted whereby the flow to the expandable bladder can be controlled or blocked.

36. The method of claim 35 wherein the gate means is initially closed so that contraction of the skeletal muscle will be unable to force fluid through the connecting means to the expandable bladder and further comprising the steps of:

allowing the formed muscle to rest for at least two weeks with the collapsible bladder in place;

thereby periodically stimulating the formed muscle for a period of 3-6 weeks; and opening the gate means all of said additional steps occurring prior to the step of periodic stimulation that compresses the aorta.

37. The method of claim 36 wherein the gate means is chosen from a group consisting of a burstable membrane, a magnetically controlled valve, and a dissolvable member.

38. The method of claim 22 further comprising the steps of:

attaching a flexible collar to the formed muscle around the cavity prior to inserting the collapsible bladder; and attaching said collar to said closed system.

39. The method of claim 22 wherein the expandable bladder is constructed of an elastic, leak-proof material.

40. The method of claim 22 wherein the collapsible bladder is constructed of a shape-retaining, leak-proof material.

41. The method of claim 22 wherein the expandable bladder located adjacent to the portion of the circulatory system abuts on only one side of said aorta.

42. The method of claim 22 wherein the expandable bladder located adjacent to the portion of the circulatory system is wrapped around said portion such that when the expandable bladder expands it exerts pressure on substantially the entire circumference of said portion.

43. The method of claim 22 wherein the sheath is made of a highly flexible, inelastic material.

44. The method of claim 22 wherein the hollow connector is substantially less elastic than either of said expandable bladder or said collapsible bladder.

45. The method of claim 22 wherein the stimulating means is an electrical pacer capable of delivering the pulse trains in synchrony with the period of the mammalian heartbeat.

46. The method of claim 22 wherein said fluid or gas is chosen to provide a preselected flow resistance between the expandable bladder and the collapsible bladder.

47. The method of claim 22 wherein said expandable bladder is constructed such that a section of said expandable bladder adjacent to a first end of said cylindrical portion will expand at a lower internal pressure than a section of said expandable bladder at a second end of said portion.

48. The method of claim 22 further comprising a means for adding or removing fluid or gas to or from the closed system.

49. The method of claim 22 wherein the entire apparatus is totally implanted.

50. The method of claim 49 wherein the muscle is formed and the apparatus is implanted in a single surgical operation.

51. The method of claim 22 further comprising the step of converting the autologous skeletal muscle to Type I muscle fiber while performing said periodic stimulation and consequent compression of said enclosed portion of the circulatory system.

52. The method of claim 51 wherein said converting is accomplished by periodic stimulation at a less than 1:1 ratio to the period of the mammalian heartbeat.

53. A method for improving the flow rate in a human blood system comprising the steps of:

forming one end of an autologous skeletal muscle pedicle of said human to create a muscle pouch having a cavity within said formed muscle pouch and leaving a second end of said muscle having a motor nerve and a primary source of blood supply attached;

attaching a flexible collar to said formed muscle pouch around said cavity;

inserting a collapsible; shape-retaining, leak-proof bladder into said cavity;

attaching said collar to said collapsible bladder;

forming a sheath around a portion of an aorta of said human and enclosing within the sheath an expandable, leak-proof bladder such that when said expandable bladder is expanded within the sheath the portion is forced to compress;

connecting said collapsible bladder to said expandable bladder using a hollow connector to form a closed system wherein the hollow connector further comprises a closed, adjustable gate means capable of being opened indirectly after the closed system is implanted;

filling the closed system with a fluid or gas;

attaching a stimulating means to said motor nerve whereby said muscle will contract upon adequate stimulation from said stimulating means;

implanting the sheath, the motor nerve, the muscle, the closed system with the fluid or gas, and the stimulating means within the human;

allowing the formed muscle pouch to rest for at least two weeks with the collapsible bladder in place;

thereafter periodically stimulating the formed muscle pouch for a period of 3-6 weeks;

opening the gate means;

stimulating said muscle periodically in synchrony with the diastole period of the heart at a rate equal to or less than a 1:1 ratio with the period of the heart, thereby making the muscle contract, collapsing the collapsible bladder, forcing the fluid or gas in said collapsible bladder through the connector and into the expandable bladder thereby expanding the expandable bladder and compressing the enclosed portion of the aorta; and alternating said periodic stimulation with periods of non-stimulation so that the muscle will cease contracting, the collapsible bladder will return to its uncollapsed state, the expandable bladder will return to its unexpanded shape, and the enclosed portion will return to its uncompressed state.

* * * * *